United States Patent
Alt

[19]

[11] Patent Number: 6,027,510
[45] Date of Patent: Feb. 22, 2000

[54] STENT DELIVERY SYSTEM

[75] Inventor: Eckhard Alt, Ottobrunn, Germany

[73] Assignee: Inflow Dynamics Inc., Arlington, Va.

[21] Appl. No.: 08/999,737

[22] Filed: Dec. 8, 1997

[51] Int. Cl.[7] ...................................................... A61F 11/00
[52] U.S. Cl. ............................................ 606/108; 606/194
[58] Field of Search ..................................... 606/108, 192, 606/194, 198, 191, 195

[56] References Cited

U.S. PATENT DOCUMENTS

| | | | |
|---|---|---|---|
| 5,599,307 | 2/1997 | Bacher et al. | 606/194 |
| 5,733,299 | 3/1998 | Sheiban et al. | 606/192 |
| 5,792,106 | 8/1998 | Mische | 606/194 |

*Primary Examiner*—Michael Buiz
*Assistant Examiner*—Kevin Truong

[57] ABSTRACT

A stent delivery system includes a catheter having a balloon mounted at its distal end for advancement into and withdrawal from a patient's vascular system by manipulation of the catheter from a point external to the patient's body, a lumen extending through the catheter into the balloon to allow the balloon to be selectively inflated and deflated from a pressurizing medium external to the patient's body, and spaced-apart radiopaque projections on the catheter adjacent the proximal and distal ends of the balloon to receive and retain a stent therebetween in overlying relation to the balloon and to provide x-ray markers thereof. The stent is deployed at a designated target site by selectively inflating the balloon to radially expand the diameter of the stent against the vascular wall. The projections are shaped (i) to protect the stent from being dislodged during travel through the vessel, but not to interfere with radial expansion of the stent during balloon inflation and (ii) to avoid injury to tissue of the vascular wall during movement of the catheter through the vessel. A method of fabricating such a stent delivery system includes providing a catheter with an elongate flexible body of size and shape suitable for traversing the vascular system and with a selectively inflatable balloon located distally on the catheter; and employing spaced-apart projections on the catheter at the ends of the balloon to retain a stent which, after the catheter is inserted through the stent, is tightly crimped onto the balloon between the projections, in readiness for radial expansion when delivered to the target site and the balloon inflated. The catheter diameter may be greater between than outside the projections, for tight crimping of the stent on the balloon, and the projections are integral with the catheter including its region of greater diameter.

12 Claims, 2 Drawing Sheets

STENT DELIVERY SYSTEM

BACKGROUND OF THE INVENTION

The present invention relates generally to stents for implantation in the body to maintain the lumen of a natural (or even artificial) vessel or duct, such as a blood vessel and specifically a coronary artery, open to allow substantially unimpeded flow through the vessel. More particularly, the invention relates to an improved system for delivering a stent to a predetermined site in the vessel for deployment against the inner surface of the vessel wall.

The benefits of angioplasty of arteries, particularly balloon angioplasty, and especially of the coronary arteries, has been amply demonstrated over the past decade. Angioplasty is effective to open occluded vessels that would, if left untreated, result in myocardial infarction (MI) or other cardiac disease or dysfunction. The benefits of the procedure are diminished, however, by restenosis rates approaching 50% of the patient population that undergo the procedure. Accordingly, a huge number of patients experiencing a successful primary percutaneous transluminal coronary angioplasty (PTCA) procedure are destined to require a repeat procedure. The patient faces an impact on his or her tolerance and well-being, as well as the considerable cost associated with repeat angioplasty.

Implantation of coronary stents in angioplasty patients has markedly reduced the complications, risks, potential MI, need for emergency bypass operation, and repeat angioplasty that are prevalent without the stenting procedure. Indeed, to reduce the likelihood of re-obstruction of the vessel at the angioplasty site, it has become common practice for the physician to implant a stent in the patient at the site of the angioplasty or atherectomy procedure, immediately following that procedure, as a prophylactic measure. The stent is advanced on a balloon catheter to the designated site of the prior (or even contemporaneous) procedure, under fluoroscopic observation. When the stent is positioned at the proper site, the balloon is inflated to expand the stent radially to a diameter at or slightly larger (in anticipation of the invariable elastic recoil of the vessel wall following stretching of the wall as a result of implantation of the stent) than the normal unobstructed inner diameter of the arterial wall, for permanent retention at the site. The implant procedure from the time of initial insertion to the time of retracting the balloon is rapid, and much less invasive than coronary bypass surgery.

The typical stent itself is composed of biologically compatible material (biomaterial) such as a suitable metal in wire mesh, wire coil or slotted tubular form. The stent should be of sufficient strength and rigidity to maintain its shape after deployment, and to resist the elastic recoil of the artery after the stent is implanted. Although improved stent structures have been developed, problems persist in the delivery systems by which the stent is implanted at the selected target site.

Successful clinical experience with stent implantation over the past few years has led to much greater use of the device. At some medical institutions, one or more stents are implanted in as many as eighty percent of all interventional procedures for angioplasty in the coronary arteries. While initially only short type AHA-ACC A-type lesions were addressed, more recently highly complex lesions are being treated by interventional strategies. Consequently, patients with multi-vessel disease, as well as those with singular vessel disease, are now candidates for successful revascularization of a narrowed coronary artery system through stenting interventional procedures, without being subjected to a major operation.

A crucial consideration for this type of revascularization is the need for exact placement of the stent at the site of the lesion. Failure to place the stent precisely at the lesion/target site is attributable to either an inability to fully distinguish the location of the stent relative to the lesion on the fluoroscope, or an inability to properly position the stent to the target site despite its viewability. Visibility (i.e., a shadow) of the position of the stent during the implant procedure is impacted by various factors despite the metallic composition of the device. An improved view is attained by providing the stent or the implanting balloon location at which it is mounted with a more distinctive radiopaque marker, or even markers at each end of the stent or at points of demarcation of its position on the balloon. Successful advancement of the stent to the target site, even with a clear view of the stent's location, may nevertheless be adversely impacted by factors such as the length and flexibility of the stent, diameter and profile characteristics of the delivery system including the balloon catheter, surface friction characteristics between the stent and the balloon on which it is mounted, anatomy of the patient, and tortuousness and roughness of the coronary system. Unfortunately, it has not been uncommon for the stent to be dislodged from the balloon or inadequately deployed during the implant procedure, making it necessary to attempt to retrieve or re-position the stent, or to implant a new stent through the improperly deployed one.

It is a principal aim of the present invention to provide a stent delivery system which enables a considerably greater likelihood of successful placement of the stent in a body vessel or duct, even in a tortuous path such as the vascular system leading to or within a coronary artery, than has previously been attained.

A non-expanded stent suitable for implantation in a coronary artery must be quite small, with a diameter less than about one millimeter (mm) and a length (typically a standard length) in a range from about seven to about thirty mm, and having characteristics that allow it to be crimped onto a balloon (either by pre-mounting by machine at the site of manufacture or manual mounting by the physician at the time of the implant procedure) and to be properly expanded in diameter during deployment. Stent structures of the slotted tube type, the coil type, or the wire mesh type are abundantly described in the prior art. Although the traditional method has been manual mounting of the stent on the balloon by the implanting physician at the time of the procedure, by crimping (involving a combination of rolling, squeezing, and compressing the stent), more recently manual mounting has been supplanted by machine mounting of the stent on the balloon at the site of manufacture for immediate use by the physician whenever the implant procedure is to be performed. Pre-mounting eliminates the requirement that the physician be specially skilled in the technique of crimping the stent without damage to the balloon, the stent itself, or capability of symmetrical expansion of the stent.

As noted above, the circumstances and environment for stent placement, particularly at a target site in the coronary vascular system marked by narrow winding arteries, increase the risk that the stent may be dislodged from its mounting balloon. Retrieving a stent which is free to move in the vascular system is a daunting task, requiring all of the skills the physician can muster, and unless accomplished quickly can have calamitous consequences of local blockage, MI and death. Therefore, it is extremely important that the stent be tightly secured to the surface of the balloon to avoid dislodgement, but without deleteriously affecting it from being readily deployed and thereafter released from the balloon at the target site.

The larger the balloon diameter, the easier it is to create friction between the surfaces for better retention of the stent on the balloon. But small diameter balloons, such as those used for PTCA, are more easily advanced through the vascular system. Most stent delivery systems in use today are rather bulky, with typical crossing diameter in the range from 1.4 to 1.6 mm. State of the art PTCA balloons are available with an outer diameter of less than 0.8 mm, which, with stent mounting, equates to a total crossing diameter of less than 1.0 mm.

Accordingly, other important aims of the invention include providing a stent delivery system and method in which the stent is either manually mounted or, preferably, pre-mounted, on the balloon catheter in a way that assures reliable retention of the stent during movement of the delivery system by advancement or withdrawal through the vessel, without interference with deployment of the stent; amenable to use of state of the art PTCA balloons; and with improved fluoroscopic observation of the location of the stent in the delivery system during travel to and placement at the selected target site.

SUMMARY OF THE INVENTION

The stent delivery system structure includes a balloon and a catheter to which the balloon is secured for advancement and withdrawal into and from a patient's vascular system. The catheter includes a lumen for passage of a fluid, such as saline solution and contrast dye, into and from the balloon for inflation and deflation thereof via a control valve external to the patient's body. Another lumen extending the length of the catheter accepts a wire for guiding the delivery system along the selected path to the target site. According to the invention, the catheter has a pair of spaced-apart projections, bumps or raised portions at the distal and proximal ends of the balloon, with spacing between the bumps (and the length of the balloon therebetween) slightly greater than the length of the stent to be implanted, to accommodate the stent in non-binding relation therebetween. The bumps may extend fully about the circumference of the catheter within bands adjacent the proximal and distal ends of the balloon, or may only partly encircle the catheter at the bands to leave a gap between portions of the bumps, including only a single bump at each end. The critical aspects of the bumps is that they be sufficiently sized and shaped to retain the stent in place on the balloon and to protect it against being dislodged while the delivery system is being advanced to (or retracted from) the target site in the vessel; and also to allow the delivery system to be moved through the smallest diameter vessel in the path to the target site without substantial injury to or binding against the vessel wall.

Instead of projections or bumps which are part of the catheter itself as by molding, they may be fabricated separately from the catheter and thereafter adhesively applied at the respective locations on the catheter by gluing with a medical grade adhesive.

According to another feature of the invention, the bumps are provided with radiopaque material to perform additionally as x-ray markers of the ends of the balloon and the stent. As a result, the location of the stent is easily visible on the fluoroscope, to allow placement and implantation exactly at the target site (e.g., the site of the lesion left after angioplasty). The radiopaque material need not occupy the whole of each bump, but should be sufficient in scope to make the stent's position nicely visible to the implanting physician.

The stent, preferably of the slotted tube type, may be mounted manually over the balloon by crimping to compress its diameter after sliding it over the bumps to occupy the space therebetween. The production size of the stent should be sufficient that its inner diameter (i.e., the diameter of its central lumen) is at least slightly larger than the diameter of the catheter at the bumps. Manual mounting is achieved by grasping the stent initially at its midsection, between the thumb and forefinger, and continually rolling and squeezing it to compress its diameter to produce a snug fit on the balloon membrane. Preferably, however, the stent is pre-mounted on the balloon catheter by machine at the factory, to eliminate a need that the implanting physician have had prior experience with crimping a stent on a balloon, or even having such experience, face solving a problem of tight crimping close to the bumps.

Consequently, the stent will be held securely on the delivery system and protected against being dislodged from the balloon during advancement or retraction thereof through the patient's vascular system to the target site.

The invention also resides in a related method for producing the stent delivery system.

The stent delivery system of the invention need not be limited to use in the vascular system, but rather, may be used for deploying a stent in any natural or artificial duct in a patient's body, such as in the esophagus, or the gastrointestinal system.

BRIEF DESCRIPTION OF THE DRAWINGS

The above and still further aims, objects, features and attendant advantages of the present invention will become apparent from a consideration of the ensuing detailed description of the presently contemplated best mode of practicing the invention, by reference to a preferred embodiment and method, taken with accompanying Figures of drawing, in which.

DETAILED DESCRIPTION OF THE PREFERRED EMBODIMENTS AND METHOD

Figure 1:
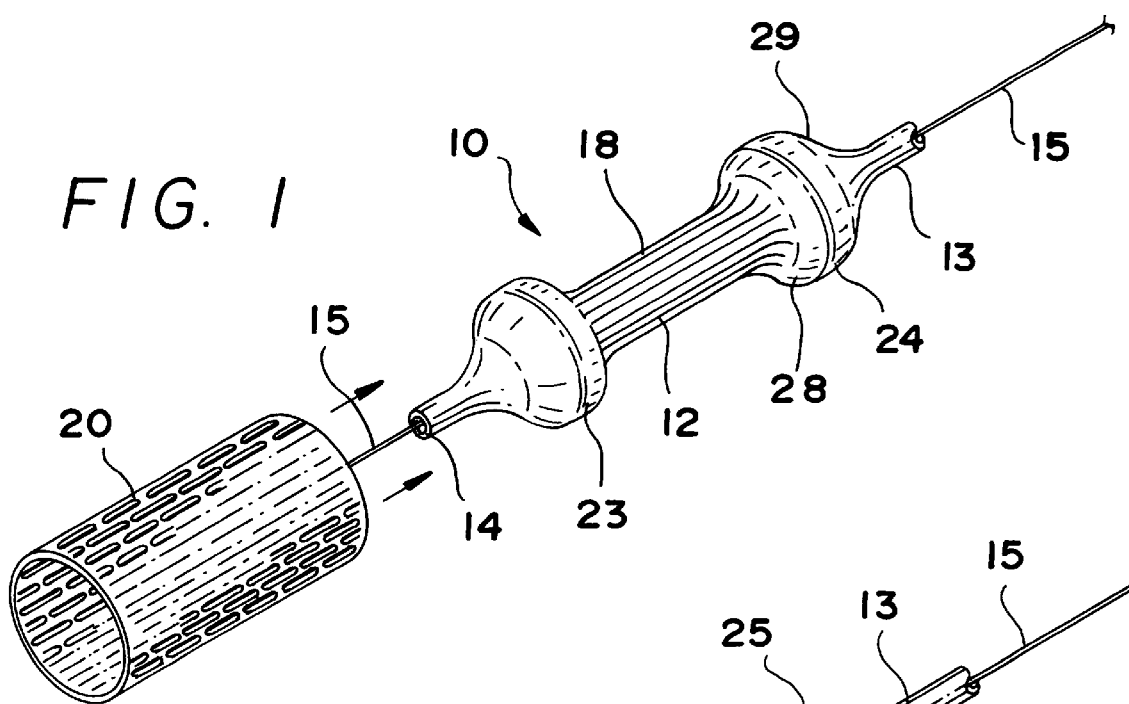
FIG. 1 is a perspective view of a portion of a stent delivery system illustrating a preferred embodiment of the invention, exploded to show the stent being moved toward its position on the balloon but not yet in place.
Figure 4:
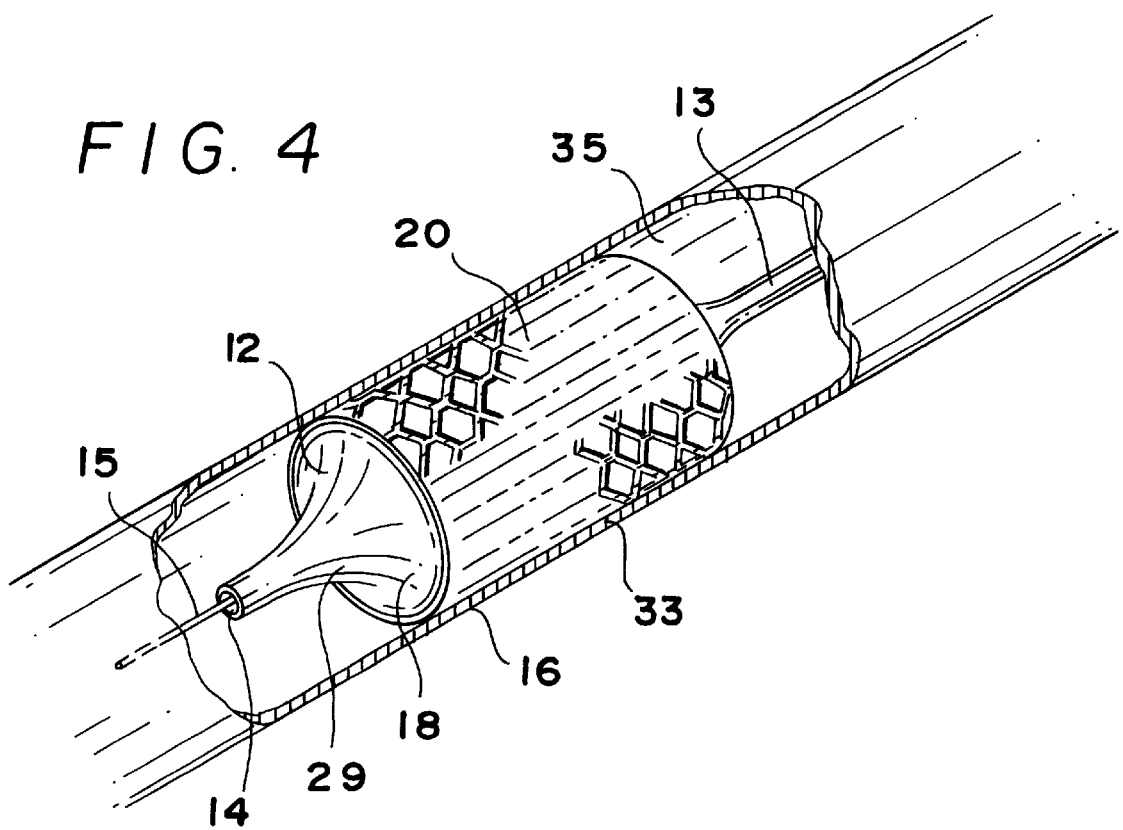
FIG. 4 is a perspective view of a stent which has been delivered to the target site in a coronary artery of the patient and is in the expanded state at that site by virtue of inflation of the mounting balloon.
Figure 5:
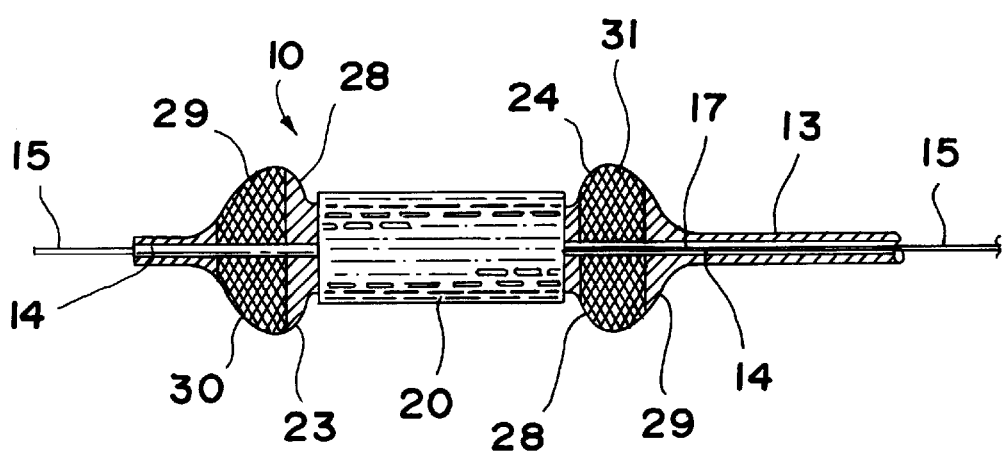
FIG. 5 is a side view of the embodiment of FIG. 1, partly in section with the stent illustrated fully in position and tightly crimped on the balloon between the bumps at either side of the balloon.

Referring now to the drawings, which are exaggerated to show details and are not to scale, a stent delivery system 10 according to a preferred embodiment of the invention shown in FIGS. 1, 4 and 5 includes a PTCA balloon 12 with an outer diameter of about one mm. The balloon is attached to the distal end of a catheter 13 with a central inner lumen 14 through which a guide wire 15 extends to aid in threading (i.e., advancing) the catheter 13 into and through the coronary artery 16 (FIG. 4) in the arterial system of a patient.

A channel 17 in the catheter, which is a separate lumen offset from the central lumen 14, is provided to allow passage of non-compressible fluid under pressure into and from the reservoir of the balloon within balloon membrane 18, from a point located external to the patient's body, to selectively inflate and deflate the balloon. The non-compressible fluid may, for example, comprise a saline solution, which is pumped under pressure into the balloon 12 when the delivery system 10 has been advanced to position a stent 20 mounted on the balloon membrane for deployment at a selected target site in the coronary artery. As illustrated in FIG. 4, the balloon membrane 18 expands when the balloon is inflated, to expand the diameter of the mounted stent until it is pressed against the inner surface of the wall of artery 16, where it remains when the membrane contracts as the balloon is deflated, to permit withdrawal of the delivery system from the patient's body.

FIG. 1 is a fragmentary exploded view in which the stent 20 is shown as being moved into position for crimping on the balloon 12 (FIG. 5) either at the time of manufacture of the stent delivery system (for a pre-mounted stent version) or at the time the delivery system is to be introduced in the arterial system of the patient for implanting the stent (for a manually crimped stent version).

Figure 2:
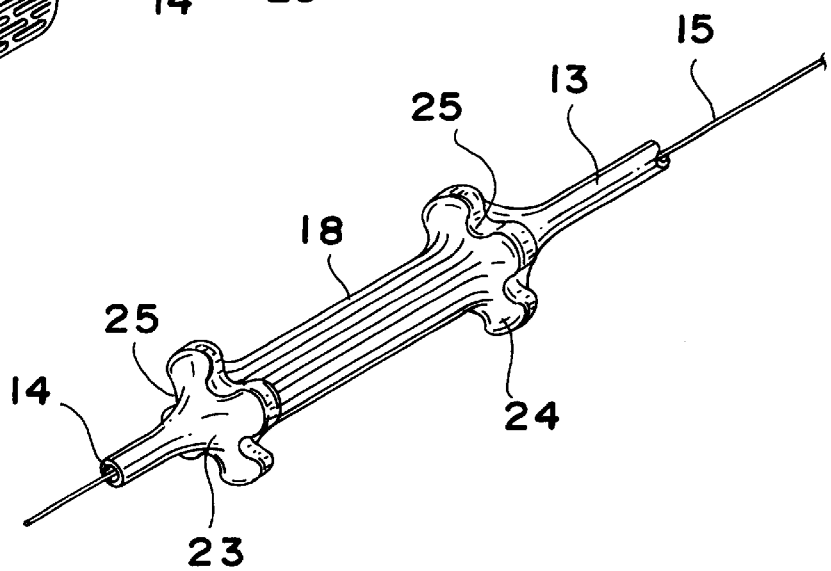
FIG. 2 is a fragmentary perspective view of an alternative embodiment.
Figure 3:
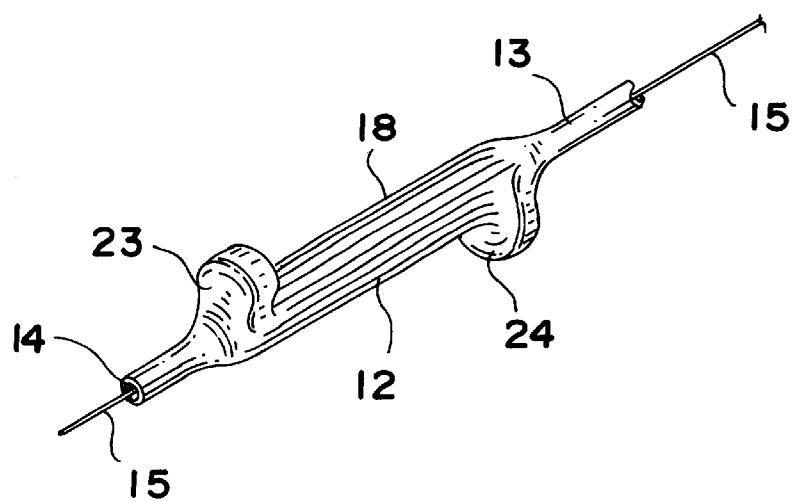
FIG. 3 is a fragmentary perspective view of another alternative embodiment of the invention.

According to the present invention, catheter 13 is fabricated with a pair of spaced-apart bumps or projections 23 and 24 at the distal and proximal ends of the balloon 12, with the spacing between the bumps (and the length of the balloon therebetween) being made at least slightly greater than the length of the stent 20 which is to be implanted, to accommodate the stent therebetween. The bumps may extend fully about the circumference of the catheter at their locations proximal and distal of the balloon ends which is the preferred embodiment as shown in FIGS. 1, 4 and 5, or may be interrupted by slots or channels 25 as shown in the alternative embodiment of FIG. 2, or may be disposed at only one or two points at those locations as shown in another alternative embodiment of FIG. 3. Although adequate space exists between the maximum circumference of the bumps in the preferred embodiment and the inner surface of the vessel (e.g., artery) wall to permit substantially unimpeded blood (or other fluid) flow, the alternative embodiments allow enhanced perfusion and still provide sufficient surface area to retain the stent in place on the balloon, particularly after the stent has been crimped in place.

In any event, the critical aspect of the bumps 23 and 24 is that they be sufficiently sized and shaped to retain the stent 20 in place on the balloon 12 without likelihood that the stent will be dislodged, while the delivery system is being advanced to (or retracted from) the target site in the vessel; and also to allow the delivery system to be moved through the smallest diameter vessel in the path to the target site with adequate protection to avoid or reduce the likelihood of the stent cutting, scraping or binding against the vessel wall. The preferred embodiment serves these purposes admirably. Also, the bumps are shaped with special attention to the inner surface 28 and outer surface 29 thereof In particular, inner surface 28 of each bump has a slope (the inner slope) which although smoothly contoured, is relatively perpendicular to the axis of the catheter, to safely secure the stent in proper position on the catheter. In contrast, the outer surface 29 of each bump has a more sloping contour (the outer slope), preferably at a nominal angle in a range of from about 30 degrees to about 60 degrees relative to the catheter's longitudinal axis, which enables the delivery system to be moved (i.e., advanced or retracted) smoothly through the vessel without a substantial risk of injury to tissue or binding against the vessel wall during movement.

While the balloon catheter 13 is preferably manufactured to have the bumps 23 and 24 at each end of the balloon, by molding the catheter from biocompatible material to include them, the bumps may instead be fabricated separately of the same conventional material as the catheter, in any conventional manner, and thereafter fixedly applied at those locations on the stent by gluing them onto the surface of the catheter with a medical grade adhesive. Of course, in the latter case, the surface of the bumps which is to contact the catheter should match the contour of the catheter at those points.

The diameter of the catheter in a plane perpendicular to its axis through and including the maximum extent of the bumps should be at least slightly less than the diameter of the stent 20 in its production state (or, if need be, in a slightly expanded state) to allow the stent to be slid over the bumps (actually, only over bump 23 as shown in FIG. 1) to a position over the catheter in which the stent occupies the space between the bumps (and thus, between the distal and proximal points of balloon 12 (as shown in FIG. 5). Also, the space between the bumps should be predetermined to match (i.e., to slightly exceed) the length of a particular stent, to readily accommodate the stent therebetween in a snug but not overly tight fit. If the fit were too tight, it could inhibit expansion of the stent because its ends could bind against the inside surface of the bumps. On the other hand, too loose a fit could preclude precise placement of the stent at the selected target site when it is to be implanted.

After the catheter has been inserted through the lumen of the stent so that the stent occupies that position, the stent is crimped to compress its diameter sufficiently that it is mounted on the balloon. The crimping must be sufficiently tight that the stent will remain physically compressed tightly against the balloon membrane 18 and thereby securely retained on the delivery catheter between the bumps 23 and 24. This will tend to assure a reliable and safe delivery of the stent system to the target vascular lesion.

If desired, the mounting of the stent onto the catheter to provide the delivery system may be postponed until the stent is to be implanted in the patient. If so, just before the implant procedure is to be performed, the stent is manually mounted onto the catheter by the implanting physician by inserting the catheter through the central lumen of the stent to occupy a position between the bumps, grasping the stent initially at its midsection between the thumb and forefinger, and rolling and continually squeezing it to compress its diameter sufficiently to render it tightly captive on the balloon membrane. Preferably, however, the stent is pre-mounted on the balloon catheter at the factory (as by machine crimping), to assure a consistently uniform and proper fit. It is preferred that the outer diameter of the crimped stent when mounted on the balloon be at least about 0.05 mm smaller than the diameter of the bumps (i.e., of the delivery catheter at the bumps). In the region between the bumps the catheter diameter may be slightly greater than its diameter proximal and distal to the bumps, so as to guarantee an even tighter fit of the crimped stent on the balloon.

Any conventional stent may be mounted in the manner described on the delivery catheter of the present invention, although a slotted tube type such as disclosed in applicant's co-pending application Ser. No. 08/933,627, filed Sep. 19, 1997, is preferred. In the Figures, the stent 20 is depicted to be of the slotted tube design. When crimped at its mounting position on the delivery catheter, the stent may have an inner lumen diameter of about 1.05 mm and an outer diameter of about 1.18 mm, for example. As a practical matter, the minimum inner lumen diameter of the crimped stent is that diameter which is technically achievable in view of the sum of the widths of all of the struts in the circumference of the stent. The maximum diameter of each bump 23 and 24 is preferably about 1.35 mm, but should always be at least about 0.05 mm larger than the outer diameter of the mounted, crimped stent.

The stent delivery system 10, which basically comprises the balloon 12, catheter 13, guide wire lumen 14, inflation duct 17, and stent 20, is initially inserted into the arterial system (or other duct of the body, depending on the site at which the stent is to be placed), via a puncture or other surgically provided opening, and is then advanced through the blood vessel(s) while the implanting physician views its progress by means of fluoroscope. In a typical procedure involving stenting after angioplasty, the delivery system is threaded through the tortuous path presented by the arterial system and, at least for a portion of the path, a guide catheter, until the stent is aligned with the section of a coronary artery wall—the target site—at which the stent is to be placed. During its advancement to position the stent at that site, the delivery system may and typically does encounter friction from the roughness of the arterial system and movement through the bloodstream, the forces being applied principally to the leading edges at the distal end of the delivery system. The shape of the leading bump (23 in the case of advancement, or 24 in the case of retraction of the delivery system), with its outer slope 29 and smooth contour, is such that the tissue or other material of the vessel wall is protected against injury, and the stent is protected against being dislodged from its position on the delivery catheter.

Despite the very minimal risk, even if the stent were to be dislodged from the delivery catheter in the case of encountering a difficult lesion during advancement of the delivery system in the arterial system, the stent would be recaptured by the leading bump (in this case, bump 24) and not lost when the catheter is retracted from the arterial system To enhance the visibility of the stent's location to the implanting physician during advancement of the delivery system for placement of the stent at the target site, the bumps 23 and 24 preferably incorporate or have applied to the surface thereof a radiopaque material of any conventional suitable type, such as at bands 30 and 31 (FIG. 5), as markers of or adjacent the ends of the stent. As a result, the location of the stent is easily visible on the fluoroscope, to allow it to be placed exactly at the target site (e.g., the site of the lesion left after angioplasty). It is not necessary that the radiopaque material occupy the entirety of each bump, but in any event it should be sufficient in scope to render the stent's position nicely visible to the implanting physician on the X-ray. In FIG. 5, radiopaque band 30 is slightly displaced from the inner surface 28 of bump 23, while radiopaque band 31 substantially commences at the inner surface 28 of bump 24. In practice, both bands would be located at the same portion of the respective bump. The purpose of the showing in FIG. 5, is simply to indicate that it does not matter what the location of the markers may be on the bumps, so long as they are identical on each, because the physician can see that they denote the location of the stent centrally between the markers.

Preferably, however, the radiopaque markers are located at the inner surface of each bump (i.e., in the case of a radiopaque band, the band commences at the inner surface) to better delineate the end points of the stent. In that respect also, the stent 20 mounting between bumps 23 and 24 of the delivery catheter in FIG. 5 is exaggerated in its showing of a separation between either end of the stent and the inner surface 28 of the respective bump. As was stated above, the spacing between the bumps should be predetermined to match (by just slightly exceeding) the length of the stent to snugly (but not tightly) accommodate the stent therebetween. This serves to better assure exact placement of the stent at the target site, and avoids binding of the stent ends against the bumps during inflation of the balloon.

When stent 20 is to be deployed at the target site (FIG. 4)—typically the site of a stenotic lesion where an artery lumen has been or is being opened by balloon or other angioplasty—the mounting balloon 12 is selectively fully inflated via duct 17, thereby causing the stent to undergo radial expansion until its outer surface engages the tissue at the inner surface of the wall 33 of artery 35 at the target site. Customarily the stent is expanded to a diameter slightly greater than the inner diameter of the arterial lumen at the target site, to slightly stretch the tissue in the wall and compensate for the expected recoil of the artery when the pressure on its inner wall is removed. This occurs after the balloon is selectively deflated to allow withdrawal of the delivery catheter from the patient's body. The stent, of course, remains in place at the target site.

The stent delivery system of the invention need not be limited to use in the vascular system, but rather, may be used for deploying a stent in any natural or artificial vessel or duct in a patient's body, such as in the esophagus, or the gastrointestinal system.

Although certain preferred embodiments and methods have been disclosed herein, it will be appreciated by those skilled in the art to which the invention pertains, from a consideration of the foregoing description, that variations and modifications may be made without departing from the spirit and scope of the invention. Accordingly, it is intended that the invention shall be limited only by the appended claims and the rules and principles of applicable law.

What is claimed is:

1. A stent delivery system for implanting a stent at a predetermined target site in a vessel in a patient's body to maintain the lumen of the vessel open at said site, comprising a catheter having an elongate flexible cylindrical body, a selectively inflatable balloon located distally on said body of the catheter and having distal and proximal ends, a pair of spaced-apart retainers composed of the same flexible material as, and projecting radially from, said body of the catheter, said retainers located at respective ones of said distal and proximal ends of the balloon and each of said retainers having an inner surface located directly adjacent its respective end of said balloon of smooth contour and substantially perpendicular to the longitudinal axis of said body of the catheter and an outer surface opposite from said inner surface also of smooth contour but of substantially more gradual slope than said inner surface, a tubular metal stent crimped onto said balloon between said retainers, said retainers projecting radially beyond the diameter of said tubular crimped stent whereby to retain said crimped stent captive therebetween protected against being dislodged from its captive position and prevented from scraping the wall of said vessel during travel of the stent delivery system through the vessel, each of said retainers including a radiopaque marker for fluoroscopic designation of said ends of the balloon and, thereby, the location of said crimped stent during said travel.

2. The stent delivery system of claim 1, wherein the respective inner surfaces of said spaced apart retainers are shaped to secure said crimped stent therebetween without interference with expansion of the diameter of the stent when the balloon is inflated.

3. The stent delivery system of claim 2, wherein the respective outer surfaces of said spaced apart retainers are shaped to allow said delivery system to traverse the vessel without injury to the wall thereof during said travel.

4. The stent delivery system of claim 1, wherein each of said retainers completely encircles the surface of said cylindrical body of the catheter in a band perpendicular to the longitudinal axis of said bode of the catheter at said distal and proximal ends of the balloon.

5. The stent delivery system of claim 1, wherein said body of the catheter has a diameter between said retainers which exceeds the diameter of the catheter proximal and distal of said spaced apart retainers, to enable a tighter fit of the stent when crimped onto the balloon.

6. A device for delivering a stent to a target site in a duct within a patient, comprising a lead composed of flexible biocompatible material and having distal and proximal ends, for traversing the duct by manipulation from outside the patient, a stent, a mounting balloon for said stent, said balloon being attached adjacent said distal end of the lead and inflatable via a lumen within the lead to enable deployment of said stent mounted thereon at said target site, and asymmetrically shaped, longitudinally spaced apart protective radiopaque projections composed of the flexible material of said lead and positioned on the lead at opposite ends of the balloon for captivity retaining said mounted stent on said lead without binding thereon and for protecting the wall of said duct from injury during travel of said device through the duct with said stent mounted on said balloon between said projections, said lead having a diameter between said spaced apart projections greater than its diameter outside said spaced apart projections to enhance crimping said stent on said balloon.

7. The device of claim 6, wherein each of the projections has a diameter which is predetermined to exceed the diameter of said stent when tightly crimped on the balloon, by at least about 0.05 millimeter.

8. The device of claim 6, wherein said stent is tightly crimped on the balloon between the spaced apart projections.

9. The device of claim 6, wherein the space between the projections exceeds the length of the stent by only an amount sufficient for a snug fit between the projections when the stent is crimped on the balloon, the radiopacity of the projections serving to designate the extremities of the stent under fluoroscopy when the lead is being manipulated to deliver the stent to the target site within the duct internally of the patient's body, whereby to enable improved positioning of the stent during deployment thereof at the target site.

10. The device of claim 6, wherein the spaced apart projections are integral with the lead.

11. A stent delivery system for implanting a stent at a predetermined target site in a vessel in a patient's body to maintain the lumen of the vessel open at said site, comprising a catheter with an elongate flexible body and a selectively inflatable balloon located distally on the catheter; and retention means integral with the catheter at each end of the balloon for mounting a stent over the balloon and for protecting the stent against being dislodged from its mounted position during travel of the delivery system through the vessel, said retention means including spaced apart projections on the catheter at distal and proximal ends of the balloon, and said catheter having a diameter between said projections which exceeds the diameter of the catheter proximal and distal of the spaced apart projections, to enable a tighter fit of the stent when crimped onto the balloon.

12. A device for delivering a stent to a target site in a duct within a patient, comprising a flexible lead having distal and proximal ends, for traversing said duct by manipulation from outside the patient, a mounting balloon for a stent, said balloon being attached adjacent said distal end of the lead and inflatable via a lumen within the lead to enable deployment of said stent at the target site, and longitudinally spaced apart protective radiopaque projections positioned on the lead at opposite ends of said balloon for protectively retaining the stent on the lead during travel through said duct when said stent is crimped onto the balloon between said projections, said lead having a diameter between said projections which exceeds the diameter of the lead outside said spaced apart projections, to enable tight crimping of said stent on the balloon between said projections.

* * * * *